(12) United States Patent
Odedra

(10) Patent No.: US 7,056,670 B2
(45) Date of Patent: Jun. 6, 2006

(54) SEQUENCING METHOD

(75) Inventor: Raj Odedra, Amersham (GB)

(73) Assignee: GE Healthcare UK Limited, Amersham (GB)

( * ) Notice: Subject to any disclaimer, the term of this patent is extended or adjusted under 35 U.S.C. 154(b) by 29 days.

(21) Appl. No.: 10/312,053

(22) PCT Filed: Jul. 2, 2001

(86) PCT No.: PCT/GB01/02981

§ 371 (c)(1),
(2), (4) Date: Mar. 25, 2003

(87) PCT Pub. No.: WO02/02813

PCT Pub. Date: Jan. 10, 2002

(65) Prior Publication Data

US 2003/0190647 A1    Oct. 9, 2003

(30) Foreign Application Priority Data

Jul. 5, 2000   (GB) ................. 0016473.1

(51) Int. Cl.
*C12Q 1/68* (2006.01)
*C12P 19/34* (2006.01)
*G01N 33/00* (2006.01)
*C07H 21/02* (2006.01)
*C07H 21/04* (2006.01)

(52) U.S. Cl. ............... 435/6; 435/91.1; 435/91.2; 436/94; 536/23.1; 536/24.3; 536/24.33

(58) Field of Classification Search .............. 435/6, 435/91.1, 91.2, 91.51, 183; 436/94; 536/23.1, 536/24.3, 24.33, 25.3, 25.32
See application file for complete search history.

(56) References Cited

U.S. PATENT DOCUMENTS

| 5,302,509 | A |   | 4/1994  | Cheeseman |     |
|-----------|---|---|---------|-----------|-----|
| 6,136,543 | A | * | 10/2000 | Anazawa et al. | 435/6 |
| 6,355,435 | B1 | * | 3/2002 | Wilson et al. | 435/6 |

FOREIGN PATENT DOCUMENTS

| WO | WO90/13666 | 11/1990 |
| WO | WO96/27025 | 9/1996 |
| WO | WO99/05315 | 2/1999 |
| WO | WO00/06770 | 2/2000 |
| WO | WO00/18956 | 4/2000 |
| WO | WO00/58507 | 10/2000 |

* cited by examiner

*Primary Examiner*—Frank Lu
(74) *Attorney, Agent, or Firm*—Yonggang Ji

(57) ABSTRACT

Disclosed is a single molecule sequencing method comprising the steps of: a) attaching a molecule to a solid phase; b) incubating the molecule with a first composition comprising a first reporter moiety; c) detecting incorporation of said first reporter moiety; d) performing a reaction to eliminate said first reporter moiety; e) incubating the molecule with a second composition comprising a second reporter moiety; f) detecting incorporation of said second reporter moiety; characterized in that the first and second reporter moieties can be distinguished from each other.

12 Claims, 3 Drawing Sheets

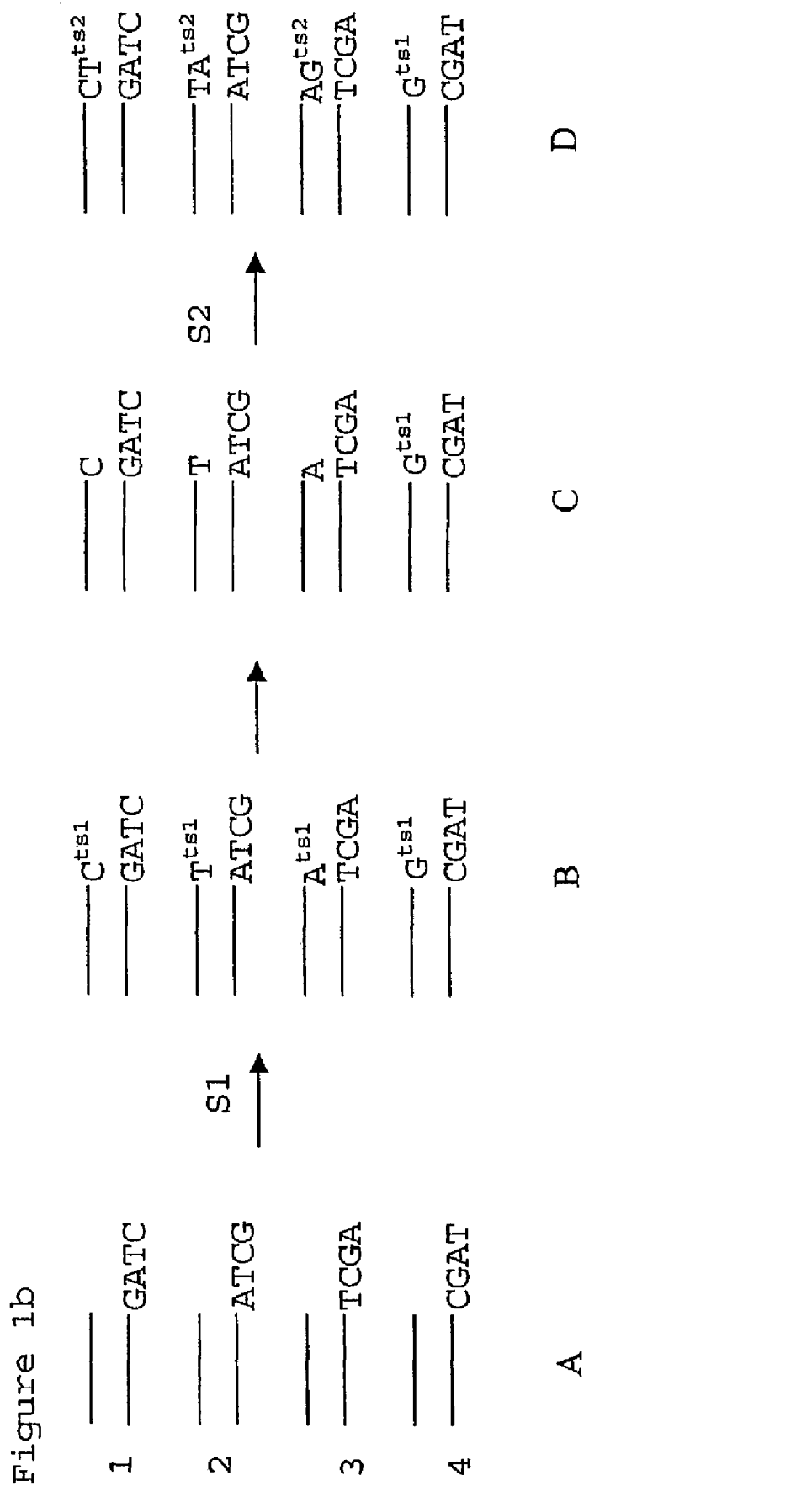

SEQUENCING METHOD

FIELD OF THE INVENTION

Figure 1A:
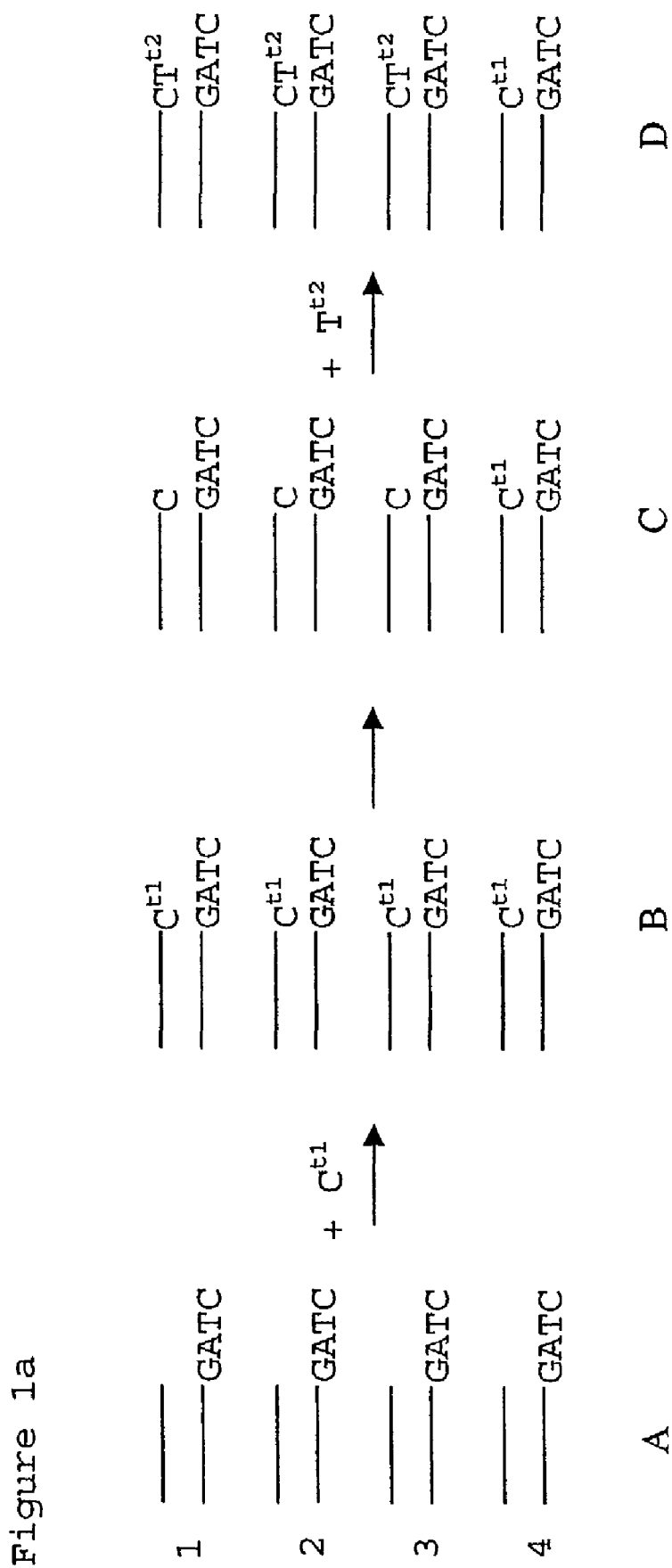

The present invention relates to a nucleic acid sequencing method and, in particular, a method that permits error correction during the sequencing of individual molecules.

BACKGROUND OF THE INVENTION

Nucleic acid sequencing is routinely performed by the method of chain termination and gel separation, essentially as described by Sanger, F., S. Nicklen, and A. Coulson (Proc Natl Acad Sci U S A, 1977. 74(12); p. 5463–7). The method relies on the generation of a mixed population of nucleic acid fragments representing terminations at each base in the sequence. The sequence is then determined by electrophoretic separation of these fragments.

Recent efforts to increase the throughput of sequencing have resulted in the development of alternative methods that eliminate the electrophoretic separation step. A number of these methods utilise base extension (i.e. base addition) and have been described for example in WO 93/21340, U.S. Pat. No. 5,302,509 and U.S. Pat. No. 5,547,839. In these methods, the templates or primers are immobilised on a solid surface before exposure to reagents for sequencing. The immobilised molecules are incubated in the presence of nucleotide analogues that have a modification at the 3' carbon of the sugar residue that reversibly blocks the hydroxyl group at that position. The incorporation of such modified nucleotides by a polymerase ensures that only one nucleotide is added during each cycle of base extension. The added base is then detected by virtue of a label that has been incorporated into the 3' blocking group. Following detection, the blocking group is removed (or 'cleaved'), typically, by photochemical means to expose a free hydroxyl group that is available for base addition during the next cycle.

Another approach to parallel sequencing has been the use of sequential elimination of nucleotides by type IIS restriction digestion (see, for example, U.S. Pat. Nos. 5,856,093, 5,599,675 and U.S. Pat. No. 5,715,330). With this method the template is rendered suitable for cohesive-end ligation. An adapter, that is substantially double stranded and contains a type IIS restriction enzyme recognition motif, is ligated to the template. The termini of these adapters that participate in ligation have one of the four bases at their end and their identity is demonstrated by a corresponding fluor on the adapter. The ligation step is dependent upon terminal base complementarity and is therefore the discriminating step. Following ligation the fluorescence is detected and the terminal base identified. The position of the type IIS recognition motif is such that cleavage by the restriction enzyme is effected one base downstream from the ligation site, exposing the next base for ligation and subsequent identification.

Generally, non-separation based approaches rely on the presence of large numbers of template molecules for each target sequence to generate a consensus sequence from a given target. Thus, for example, base extension reactions may be applied to multiple templates by interrogating discrete spots of nucleic acid, each comprising a multiplicity of molecules, immobilised in a spatially addressable array.

However, reactions of terminator incorporation/cleavage, or base excision are prone to errors. For example, as described above, base extension strategies have generally utilised nucleotide analogues that combine the functions of a reporter molecule, usually a fluor, with that of a terminator occupying the 3' position on the sugar moiety. The bulky nature of the group and its position renders these compounds highly inefficient substrates for polymerases. In addition, the cleavage of the terminator group to permit subsequent additions is also subject to inefficiencies. In the presence of thousands, or preferably millions, of molecules for each target, even modest errors of less than 5% result in a cumulative loss of synchrony, between the multiplicity of strands representing each molecule, within a small number of cycles. Thus, with each cycle of sequencing the background noise increases progressively with a consequential deterioration of signal with each addition. This means that the number of bases of sequence data that can be obtained is limited before the specific signal becomes indistinguishable from background.

Recent advances in methods of single molecule detection (described, for example, in Trabesinger, W., et al., Anal Chem., 1999. 71(1); p. 279–83 and WO 00/06770) make it possible to apply sequencing strategies to single molecules. However, sequencing, when applied to clonal populations of molecules, is a stochastic process that results in some molecules undergoing reactions while others remain unmodified. Thus, in conventional sequencing methods, errors such as mis-incorporations are not normally of serious significance as the large numbers of molecules present ensure that consensus signal is obtained. When these reactions are applied to single molecules the outcomes are effectively quantized.

One such single molecule sequencing method is based on base excision and described, for example, in Hawkins, G. and L. Hoffman, Nature Biotechnology, 1997. vol.15; p. 803–804 and U.S. Pat. No. 5,674,743. With this strategy, single template molecules are generated such that every base is labelled with an appropriate reporter. The template molecules are digested with exonuclease and the excised bases are monitored and identified. As these methods use highly processive enzymes such as Lambda exonuclease, there is the potential for analysing large templates of several kilobases in length. However, the continuous monitoring of excised bases from each template molecule in real time limits the number of molecules that can be analysed in parallel. In addition, there are difficulties in generating a template where every base is labelled with an appropriate reporter such that excised bases can be detected on the basis of intrinsic optical or chemical properties.

Methods based on base extension (such as BASS) have also been adapted to a single molecule approach.

However, these techniques are prone to errors. In particular, incorporation of modified nucleotides can fail, for example, as the result of decreased efficiency of polymerase action with modified nucleotides. Where the reporter molecule is a fluorescent molecule, errors can also occur through failure of fluorescence because the fluor is lost, damaged, bleached, or unexcited. Importantly, a failure of elimination of a reporter molecule before the next cycle of sequencing begins may result in carryover of a reporter from a preceding cycle leading to a false base call. This can occur through failure to remove a terminator and/or reporter molecule (e.g. in a cleavage reaction). At the single molecule level, failures such as these will result in a failure in obtaining adequate sequence.

SUMMARY OF THE INVENTION

It is an object of the present invention to provide a single molecule sequencing method that enables errors to be detected. It is a further object of the present invention to allow analysis and error prevention, or correction, by monitoring the fate of individual molecules through sequencing reactions.

Accordingly, in a first aspect of the invention, there is provided a single molecule sequencing method comprising the steps of:

a) attaching a molecule to a solid phase b) incubating the molecule with a first composition comprising a first reporter moiety c) detecting incorporation of said first reporter moiety d) performing a reaction to eliminate said first reporter moiety e) incubating the molecule with a second composition comprising a second reporter moiety f) detecting incorporation of said second reporter moiety characterised in that the first and second reporter moieties can be distinguished from each other.

Methods for deposition and fixation of molecules onto solid phases are well known in the art. Methods of attaching nucleic acids, for example, are reviewed in Schena (ed.), DNA Microarrays: A practical approach, Oxford University Press (1999) ISBN: 0199637768. Typically, the solid phase will be glass such as a glass slide, although other materials such as amorphous or crystalline silicon or plastics can be used.

In one embodiment, a plurality of molecules can be attached to the solid phase in an ordered array. In an alternative embodiment, a plurality of molecules can be attached to the solid phase in a random distribution. A random distribution on a solid phase such as a glass slide may comprise any number of molecules, preferably distributed at a density appropriate for optical resolution of sequence information. In a preferred embodiment, molecules are distributed at a density of approximately 1 molecule per 0.1 to 100 $\mu m^2$ and, most preferably, 1 molecule per 0.1 to 10 $\mu m^2$.

In one embodiment, the molecule can be a nucleic acid molecule, which is, preferably, at least partially double stranded. In a preferred embodiment, the molecule can be DNA and, preferably, a complex of a primer and a template. The complex of primer and template can be preformed by incubation under appropriate hybridisation conditions before immobilising the complex onto a solid phase. Alternatively, the primer or the template can be immobilised onto a solid phase prior to formation of the complex by introduction of the appropriate hybridisation partner (i.e. template or primer, respectively). In yet another embodiment, the complex immobilised onto the solid phase can be a single nucleic acid molecule comprising both "primer" and "template"; for example, the immobilised polynucleotide can be a hairpin structure.

In a preferred embodiment, the first and second compositions comprise at least one nucleotide or polynucleotide. In a particularly preferred embodiment, the first and second reporter moieties in the respective first and second compositions will be incorporated into the at least one nucleotide or polynucleotide comprised therein. Thus the incorporation of the reporter moiety from the first and/or the second composition will allow the identity of an incorporated nucleotide or polynucleotide to be determined. In a particularly preferred embodiment, the first reporter moiety labels one nucleotide or polynucleotide in the first composition whereas the second reporter moiety labels a different nucleotide or polynucleotide in the second composition. Thus each template base may be queried individually with nucleotides having a different reporter moiety in two consecutive rounds of sequencing.

Suitable nucleotides or bases include purines or pyrimidines and, in particular, any of the natural bases A, C, G and T, their analogues or modified variants thereof. Suitable polynucleotides include adapter molecules, such as those which may be used in a ligation/restriction enzyme-based sequencing approach (described, for example in U.S. Pat. Nos. 5,856,093, 5,599,675 and U.S. Pat. No. 5,715,330), in which the termini of the adapter molecule is one of the natural bases, A, C, G and T, their analogues or variants thereof. A reporter moiety may be incorporated at any position in the polynucleotide.

The sequencing method may be performed by querying each template base sequentially. In its simplest form this requires that two out of the four natural bases (or their analogues) are labelled with one reporter and the remaining two are labelled with a second reporter that is distinguishable from the first. The bases are queried so that two nucleotides bearing the same reporter are not queried consecutively.

In a preferred embodiment of the first aspect, there is provided a method for single molecule nucleic acid sequencing comprising the steps of a) attaching a primer/template complex to a solid phase b) incubating the primer/template complex in the presence of a first composition comprising at least one reporter moiety and a polymerase c) detecting incorporation of said first reporter moiety d) performing a reaction to eliminate said first reporter moiety e) incubating the primer/template complex in the presence of a second composition comprising a second reporter moiety and a polymerase f) detecting incorporation of said second reporter moiety characterised in that the first and second reporter moieties can be distinguished from each other.

Suitable polymerases are enzymes that perform template-dependent base addition including DNA polymerases, reverse transcriptases and RNA polymerases. Particularly preferred are those polymerases lacking exonuclease activity. Suitable polymerases include but are not limited to T7 polymerase, Thermosequenase II, Taq DNA polymerase, the Klenow fragment of *E. coli* polymerase which lacks 3'–5' exonuclease activity, Sequenase™, φ29 DNA polymerase, exonuclease-free Pfu or exonuclease-free Vent™ polymerase.

The use of different compositions comprising detectable nucleotides permits the identification of reporter moieties incorporated in the current round of sequencing and those that have remained from a previous cycle, for example, where a reaction to eliminate the previous reporter moiety (such as a cleavage reaction) has failed to remove the reporter moiety.

The use of distinguishable reporter moieties in, at least, the first and second compositions ensures that the same reporter moiety does not participate in a sequencing reaction in two consecutive cycles of sequencing. Thus, errors such as false base calling can be eliminated as carryover of reporter moieties from a previous cycle can be detected and taken into account during sequence assembly.

Accordingly, in one embodiment, the method in accordance with the first aspect of the invention is a method for detecting errors in a sequencing reaction.

In another embodiment the sequencing method further comprises the steps:

g) incubating the molecule in the presence of a further composition comprising a further reporter moiety; and h) detecting incorporation of said further reporter moiety characterised in that any further reporter moiety can be distinguished from either the first or the second reporter moiety.

In another embodiment the template may be incubated with a total of four compositions wherein each composition comprises a different nucleotide or polynucleotide labelled with a different reporter moiety.

In a preferred embodiment, each composition comprises at least two labelled nucleotides wherein different reporter moieties label different bases and the reporter moieties in the first composition are distinguishable from each other and from those in the second composition. In a particularly preferred embodiment, each composition comprises a set of nucleotides, each set comprising all four natural bases, (their analogues or modified variants thereof), A, C, G and T, labelled with different reporter moieties for each base. Advantageously, simultaneous querying of multiple bases will permit a more rapid throughput. In a particularly preferred embodiment, the 4 bases in the first set are distinguishable from each other and from each of the 4 bases in the second set. Thus, in this embodiment, there would be a total of eight distinguishable reporter moieties.

The greater the number of sets of nucleotides which can be distinguished from other sets by virtue of comprising nucleotides labelled with distinguishable reporters, it becomes less likely that a false base call will occur into the next repeated use of the same set of reporters. For example, if only two sets of reporters are used, the probability that a reporter from the first set will be carried over for two subsequent cycles (and thus still present when the use of the first set is repeated) is higher than if, for example, four sets of reporters are used (as it is less likely that a reporter will be carried over for three subsequent rounds of cycles).

The nature of the reaction used in method step d) depends on the nature of the sequencing method. In one embodiment, the reporter moiety will be removed from the incorporated nucleotide. Methods for removing such a reporter moiety will depend on the nature of attachment of the reporter moiety to the nucleotide. Previously described methods of cleavage include photochemical cleavage or cleavage by enzymatic action. In another embodiment, the incorporated nucleotide itself may be removed.

Typically, the efficiency of cleavage of a reporter moiety will not be 100%. However, even a cleavage efficiency of 99% would lead to an undesirable level of errors with 1% of incorporated bases being carried over to the next cycle. i.e. the probability of a false base call would be 1%. As shown in the following table, by using more than one set of nucleotides comprising at least one reporter labelled nucleotide should reduce the probability of false calls arising. Thus, for example, where the cleavage efficiency is 99%, the use of two sets of nucleotides will reduce the probability of a false base call to 0.01%. Increased cleavage efficiency will lead to a further decreased probability.

| Cleavage efficiency | False calls with 1 set of reporters (%) | False calls with 2 sets of alternating reporters (%) | False calls with 3 sets of alternating reporters (%) |
| --- | --- | --- | --- |
| 99.99% | 0.01 | $10^{-6}$ | $10^{-14}$ |
| 99.9% | 0.1 | $10^{-4}$ | $10^{-10}$ |
| 99.5% | 0.5 | $2.5 \times 10^{-3}$ | $6.25 \times 10^{-10}$ |
| 99% | 1 | 0.01 | $10^{-6}$ |
| 90% | 10 | 1 | .0001 |

Those skilled in the art will also be aware of the decrease in fidelity of polymerases when only one base is present in the reaction (as described in WO 93/21340). It is therefore preferable to query all four bases simultaneously. Accordingly, in another preferred embodiment, each set of nucleotides comprises each of the four natural bases or their analogues.

A suitable reporter moiety may be any one of various known reporting systems. It may be a radioisotope by means of which the incorporated nucleoside analogue is rendered easily detectable, for example $^{32}P$, $^{33}P$, $^{35}S$ incorporated in a phosphate or thiophosphate or H phosphonate group or alternatively $^{3}H$ or $^{14}C$ or an iodine isotope. It may be an isotope detectable by mass spectrometry or nuclear magnetic resonance (NMR). It may be a signal moiety e.g. an enzyme, hapten, fluorophore, chromophore, chemiluminescent group, Raman label, electrochemical label, or signal compound adapted for detection by mass spectrometry.

In a preferred embodiment, the reporter moiety has fluorescent properties and can be detected using a sensitive fluorescence detector. It may be a fluorophore, for example, selected from fluoresceins, rhodamines, coumarins, BODIPY™ dyes, cyanine dyes and squarate dyes (described, for example, in WO 97/40104).

The properties of fluorophores can be varied to obtain distinguishable reporters. Most notably, it is possible to discriminate between fluors on the basis of emission wavelength and excitation wavelength. In a particularly preferred embodiment, where each of two sets of nucleotides comprises four reporters, eight fluorophores, each with a distinct and spectrally resolvable fluorescence emission wavelength, are used.

The Cyanine dyes (sometimes referred to as "Cy dyes™"), described, for example, in U.S. Pat. No. 5,268,486, is a series of biologically compatible fluorophores which are characterised by high fluorescence emission, environmental stability and a range of emission wavelengths extending into the near infra-red which can be selected by varying the internal molecular skeleton of the fluorophore.

The excitation (Abs) and emission (Em) characteristics of the unmodified dye molecules are shown:

| Dye | Fluorescence Colour | Abs (nm) | Em (nm) |
| --- | --- | --- | --- |
| Cy2 | Green | 489 | 506 |
| Cy3 | Orange | 550 | 570 |
| Cy3.5 | Scarlet | 581 | 596 |
| Cy5 | Far red | 649 | 670 |
| Cy5.5 | Near-IR | 675 | 694 |
| Cy7 | Near-IR | 743 | 767 |

Importantly, this means that cyanine-based dyes can be distinguished from any of the conventional dyes which give a fluorescence readout in the blue/green region of the spectrum. Measurements can be made simultaneously using two different wavelengths; for example, fluorescein-based molecules could be detected at Abs 488/Em 510 whereas reduced cyanine-based molecules, such as those based on Cy5, could be detected at Abs 649/Em 670.

The reporter moiety may comprise a signal moiety and a linker group joining it to the remainder of the molecule, which linker group may be a chain of up to 30 bond lengths and may include atoms selected from carbon, nitrogen, oxygen and sulphur atoms. The linker group may be rigid or flexible, unsaturated or saturated, as is well known in the field.

Other properties of fluorescence may be used to distinguish between the two sets of reporters and between any different reporters in each set.

Fluorescence lifetime is one such property and is described, for example, in U.S. Pat. No. 6,007,984, Nasir, M. and M. Jolley, Combinat. Chem. & High Throughput Screening, 1999. 2: p. 177–90 and Ha, T., et al., J. Phys Chem B, 1999. 103: p. 6839–6850. Chemical modifications to fluorescent reporters can yield molecules that have spectrally unresolvable emission wavelengths, but have measurably different fluorescence lifetimes. Lifetime measurements afford an additional advantage of removing background fluorescence and Raman scattering.

Fluorophores can also be chemically modified such that the polarity of the emitted light can be varied. Typically, fluorophores can freely rotate, or 'tumble', and as they will tend to be in a random orientation, they will tend to emit non-polarised light. When, however, this rotation is constrained either by introducing rigidity in the chemical structure through additional chemical bonds (for example, by using a rigidised linker), or through non-covalent binding events, polarity is introduced in the light these molecules emit. This property is extensively utilised in biomolecular analysis (see Rabinovich, E., et al., Rev. Scientific Instruments, 2000. 71: p. 522–529., Sailer, B., J. Steinkamp, and H. Crissman, Eu. J. Histochem., 1998. 122: p. 657–660, Chen, J. and P. Selvin, J. Am. Soc. Chem., 2000. 71: p. 522–529). and has the potential for discriminating two fluors that have the same emission wavelengths, but differ in the degree of polarisation of the light they emit.

Other properties in the reporter moiety that can be utilised include differences in absorbance, chemiluminescence or electrochemical properties.

Each sequencing step will result in the attachment of reporter molecules to individual templates and the detection of the reporter moiety incorporated will permit the identity of the base to be assigned. In the case of fluorescent reporters, these molecules will then be identified by, for example, fluorescence microscopy (e.g. using a photomultiplier tube (PMT) or charge coupled device (CCD)) and the fluorescence property of the reporter will permit the assignment of identity to the base incorporated in the sequencing reaction. In a particularly preferred embodiment, fluorescence events occurring to each molecule can be detected using an optical microscope linked to a sensitive detector, resulting in a distinct signal for each molecule.

In order to collect data from sequential rounds of sequencing cycles the template must be located. This would make it possible to monitor the state of each template molecule following all subsequent events during cycles of sequencing. Subsequent failure of addition, for example, manifests itself by lack of fluorescence at a location known to contain a template. Failure of the reporter due either to a lack of stimulus, or chemical damage can also be determined once the location of the template has been determined. These failed reactions can be tracked and treated in the final sequence as potential gaps due to reporter failure. If these molecules resume participation in subsequent cycles this, too, can be tracked and a meaningful sequence obtained. Individual points of single base gaps can be identified and, where multiple identical sequences have been arrayed onto the solid surface, a consensus sequence can be built up through comparisons with reference strands such as sequences of other copies of templates in the sequencing array. Alternatively single base gaps may be identified by comparison with a reference strand which may be the known sequence e.g. in the application of this technique to mutation detection.

Accordingly, in one embodiment, the template may be located concurrently with the first cycle of sequencing where the reporter molecule in the first base identifies template location. In another embodiment, the molecule (such as a template and/or primer) may itself be labelled with a reporter moiety such that its location on the solid phase may be detected in advance of the sequence cycling reaction. In one embodiment, the reporter moiety on the template will be chosen such that it is distinct from any of the reporter moieties present in, at least, the first set of nucleotides introduced into the sequencing reaction. In a particularly preferred embodiment, the reporter moiety for locating the template will be distinguishable from the reporter moieties in any of the sets of nucleotides. This would allow coincident fluorescence detection as a means of identifying the location of templates and reporter moieties incorporated by the polymerase.

Figure 2:
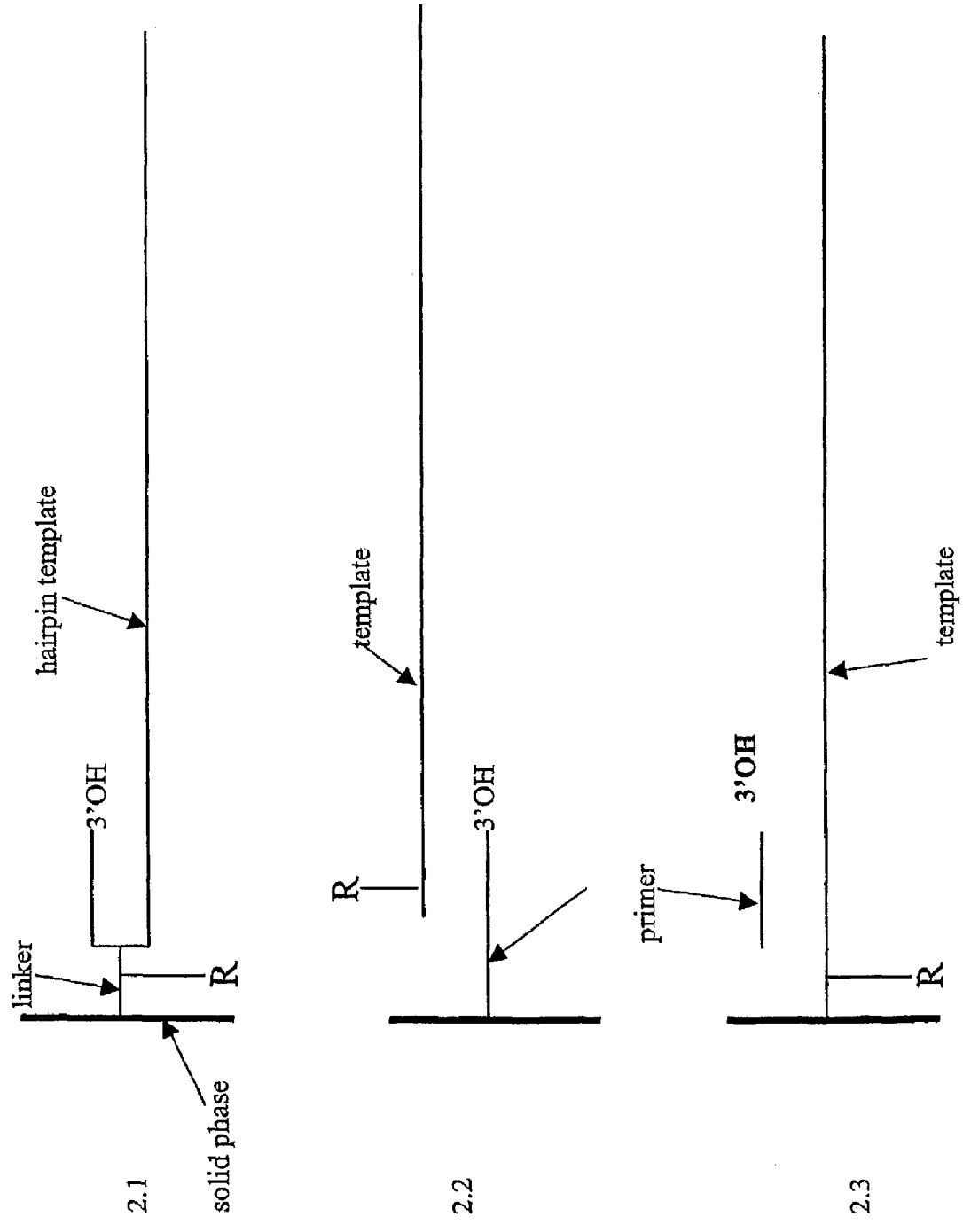

Examples of suitable attachment strategies are set out in FIG. 2. In one embodiment, the primer/template may be combined in a single molecule such as a hairpin primer, for example. In this embodiment, a reporter moiety, R, may be attached to a linker on the hairpin at its point of attachment to the solid phase. In another embodiment, the template may be labelled with a reporter moiety, R, at its 5' end. In this embodiment, either the primer or the template may be attached to the solid surface. In one embodiment the reporter moiety may be a fluorophore.

In second aspect of the invention, there is provided a method of detecting errors in a sequencing reaction comprising the steps of
 a) attaching a molecule to a solid phase
 b) incubating the molecule with a first composition comprising a first reporter moiety
 c) detecting incorporation of said first reporter moiety
 d) performing a reaction to eliminate said first reporter moiety
 e) incubating the molecule with a second composition comprising a second reporter moiety
 f) detecting incorporation of said second reporter moiety and detecting presence of said first reporter moiety as an indication of a false base call characterised in that the first and second reporter moieties can be distinguished from each other and wherein the presence of the first reporter moiety after the elimination step d) is indicative of an error.

In a third aspect, there is provided a kit for a nucleotide sequencing method in accordance with the first aspect. Preferably said kit comprises a first set of nucleotides comprising at least one nucleotide labelled with a reporter moiety and a second set of nucleotides comprising at least one nucleotide labelled with a reporter moiety characterised in that the reporter moiety in the first set of nucleotides is distinguishable from that in the second set.

SPECIFIC DESCRIPTION

For the purposes of clarity, certain embodiments of the present invention will now be described by way of example with reference to the following figures:

FIG. 1a is a diagram showing a base extension reaction where each base is queried individually. Sequence GATC is Seq. ID No. 1.

FIG. 1b is a diagram showing a base extension reaction in which all four bases are queried simultaneously. Sequence GATC is Seq. ID No. 1; sequence ATCG is Seq. ID No. 2; sequence TCGA is Seq. ID No. 3; and sequence CGAT is Seq. ID No. 4.

FIG. 2 shows examples of ways of attaching template molecules to a solid surface such that their location can be determined.

FIG. 1a demonstrates the results of a failure of cleavage in a base extension reaction. Briefly, the reaction is carried out as follows. A glass slide is coated with, for example, a silane such that thiol groups can bind a primer via phosphothioate linkage. The attached primer is contacted with a template molecule. FIG. 1a is a schematic showing four primer/template complexes (labelled 1–4) where the four complexes are identical. In step A, the template is queried with a first labelled base, $C^{r1}$ (where $^{r1}$ indicates a first reporter moiety). Step B indicates the incorporation of the labelled base into the synthesised strand. This incorporation can be read by detecting the presence of the reporter moiety, $^{r1}$. The reaction mix is then treated so as to cleave the reporter moiety from the incorporated bases. Step C demonstrates an incomplete cleavage reaction has occurred in the primer/template complex numbered 4. The reaction mix is then queried with a second labelled base, $T^{r2}$ (where $^{r2}$ indicates a second reporter moiety which can be distinguished from $^{r1}$. Step D shows the incorporation of $T^{r2}$ into primer/template complexes 1–3 while the carryover of $^{r1}$ in complex 4 is easily identifiable as $^{r1}$ is distinguishable from $^{r2}$.

FIG. 1b shows primer/template complexes, essentially as shown in FIG. 1a, but where each of the complexes 1–4 has different sequences. Here, the first round of base querying is by a first set, S1, of four bases each labelled with non-overlapping reporter moieties. Step B indicates that the 4 labelled bases are incorporated and can be detected. Following a cleavage reaction, step C indicates that reporter cleavage has failed in primer/template complex 4 where a reporter moiety from the first set of nucleotides, tS1, remains. The second base incorporation reaction is the incorporation of a second set of four bases, S2, each labelled with a reporter moiety such that they are distinguishable from each other and from the reporters used in SI. When the resulting incorporation, shown in step D are detected, the carryover of the failed cleavage, tS1, is readily identifiable. This allows the lack of cleavage in an earlier cycle to be distinguished from the incorporation of a base in the second cycle. The two sets S1 and S2 are alternated during sequencing.

FIG. 2 shows three examples of possible strategies for incorporating a label into the primer/template complex such that the position of the complex may be determined. 2.1 shows a hairpin template attached to a solid phase through a linker molecule which incorporates a reporter moiety, R. 2.2 shows a primer attached to a solid phase. The template is labelled with a reporter moiety, R, at its 5' end and, in turn, attached to the primer through hybridisation or, possibly, crosslinking. 2.3 shows a labelled template having a reporter moiety, R, at its 5' end bound to a solid phase. The primer can then be attached to the template through hybridisation. Where necessary, the primer template complex is made permanent by chemical crosslinking.

What is claimed is:

1. A method of detecting errors in a sequencing reaction comprising the steps of
   a) attaching one or more molecules to a solid phase;
   b) incubating the molecule with a first composition comprising a first reporter moiety;
   c) detecting incorporation of said first reporter moiety;
   d) performing a reaction to cleave said first reporter moiety;
   e) incubating the molecule with a second composition comprising a second reporter moiety wherein the first and second reporter moieties can be distinguished from each other; and
   f) detecting incorporation of said second reporter moiety and detecting presence of said first reporter moiety as an indication of a false base call wherein the presence of the first reporter moiety after step d) is indicative of an error.

2. The method of claim 1, wherein the one or more molecules are attached to the solid phase in a random distribution.

3. The method of claim 1, wherein the molecule is a nucleic acid molecule.

4. The method of claim 3, wherein the first and second compositions include at least one nucleotide or polynucleotide.

5. The method of claim 4, wherein the first reporter moiety labels one nucleotide or polynucleotide in the first composition and the second reporter moiety labels a different nucleotide or polynucleotide in the second composition.

6. The method of claim 4, wherein the nucleotides are purines.

7. The method of claim 4, wherein the polynucleotides are adapter molecules.

8. The method of claim 1 further comprising the steps
   a) incubating the molecule in the presence of a further composition comprising a further reporter moiety; and
   b) detecting incorporation of said further reporter moiety wherein the further reporter moiety can be distinguished from either the first or the second reporter moiety.

9. The method of claim 1, wherein each composition comprises at least two labelled nucleotides wherein different reporter moieties label different bases and the reporter moieties in the first composition are distinguishable from each other and from those in the second composition.

10. The method of claim 1, wherein each composition comprises all four natural bases, A, C, G and T, or analogues thereof, each labelled with a different reporter moiety.

11. The method of claim 1, wherein the molecule is labelled with a reporter moiety such that its location on the solid phase is detected.

12. The method of claim 1, wherein incorporation of a reporter moiety is detected using an optical microscope linked to a sensitive detector, resulting in a distinct signal for each molecule.

* * * * *

SEQUENCE LISTING

<160> NUMBER OF SEQ ID NOS: 4

<210> SEQ ID NO 1
<211> LENGTH: 4
<212> TYPE: DNA
<213> ORGANISM: artificial sequence
<220> FEATURE:
<223> OTHER INFORMATION: synthetic oligonucleotide

<400> SEQUENCE: 1 gatc                                                                   4

<210> SEQ ID NO 2
<211> LENGTH: 4
<212> TYPE: DNA
<213> ORGANISM: artificial sequence
<220> FEATURE:
<223> OTHER INFORMATION: synthetic oligonucleotide

<400> SEQUENCE: 2 atcg                                                                   4

<210> SEQ ID NO 3
<211> LENGTH: 4
<212> TYPE: DNA
<213> ORGANISM: artificial sequence
<220> FEATURE:
<223> OTHER INFORMATION: synthetic oligonucleotide

<400> SEQUENCE: 3

```
                                -continued
tcga                                                                    4

<210> SEQ ID NO 4
<211> LENGTH: 4
<212> TYPE: DNA
<213> ORGANISM: artificial sequence
<220> FEATURE:
<223> OTHER INFORMATION: synthetic oligonucleotide

<400> SEQUENCE: 4 cgat                                                                    4
```